United States Patent
Holms

(10) Patent No.: US 6,849,596 B1
(45) Date of Patent: Feb. 1, 2005

(54) REGULATORY/UNFOLDING PEPTIDES OF EZRIN

(76) Inventor: Rupert Donald Holms, 66 Regents Park Rd., London NW1 7SX (GB)

( * ) Notice: Subject to any disclaimer, the term of this patent is extended or adjusted under 35 U.S.C. 154(b) by 0 days.

(21) Appl. No.: 09/856,070

(22) PCT Filed: Sep. 15, 2000

(86) PCT No.: PCT/GB00/03566

§ 371 (c)(1), (2), (4) Date: May 17, 2001

(87) PCT Pub. No.: WO01/25275

PCT Pub. Date: Apr. 12, 2001

(30) Foreign Application Priority Data

Sep. 17, 1999 (GB) .............................................. 9921881

(51) Int. Cl.[7] ........................ A61K 38/00; A61K 49/00; C07K 11/00; C07K 14/00

(52) U.S. Cl. ............................... 514/2; 514/12; 514/13; 514/14; 514/17; 530/324; 530/326; 530/327; 530/330; 530/334; 530/344; 424/9.1; 424/184.1; 424/188.1; 424/208.1

(58) Field of Search ............................... 514/2, 12, 13, 514/14, 17; 530/324, 326, 327, 330, 334, 344; 424/184.1, 188.1, 208.1, 9.1

(56) References Cited

U.S. PATENT DOCUMENTS 5,773,573 A 6/1998 Holms
6,399,584 B1 * 6/2002 Arpin et al. ................... 514/44

FOREIGN PATENT DOCUMENTS

| GB | 2 290 293 | 12/1995 |
|---|---|---|
| WO | WO 95/33768 A1 | 12/1995 |
| WO | WO 97/12975 A1 | 4/1997 |
| WO | WO 99/47150 A2 | 9/1999 |

OTHER PUBLICATIONS

Gould, Kathleen L. et al., "cDNA cloning and sequencing of the protein–tyrosine kinase substrate, ezrin, reveals homology to band 4.1" *The EMBO Journal* (1989), pp. 4133–4142, vol. 8, No. 13.

* cited by examiner

Primary Examiner—Jon P. Weber
Assistant Examiner—Chih-Min Kam
(74) Attorney, Agent, or Firm—Saliwanchik, Lloyd & Saliwanchik

(57) ABSTRACT

This invention describes novel charged molecules which specifically bind to the Hepreceptor, a regulatory site which I have discovered in human ezrin. My invention is that when peptides or other charged molecules bind to the Hepreceptor, medically useful immune responses are induced. These charged molecules can be administered orally and by other routes for the treatment of various infectious diseases and cancer. I have determined that the Hepreceptor (human ezrin 308–373) comprises of two adjacent alpha helical domains which are folded together at a hinge region (M339–M340) and stabilised by complimentary side chain charges of the primary amino acid sequence in the soluble cytoplasmic conformation of ezrin. I have determined that in the unfolded membrane associated conformation of ezrin, the Hepreceptor is pushed through the cell membrane and is exposed on the outer surface of the cell. Hepreceptor-Domain A (amino acid numbers 308–339 of human ezrin), comprises of the following 32 amino acid sequence. SEQ ID 1 AREEKHQKQLERQQLETEKKRRETVEREKEQM Hepreceptor-Domain B (amino acid numbers 340–373 of human ezrin), comprises of the following 34 amino acid sequence (Tyrosine 353 [Y] may be phosphorylated to phosphotyrosine [Yp] in the membrane associated conformation of ezrin): SEQ ID 2 MREKEELMLRLQDY(p)EEKTKKAERELIEQIQRALQ.

20 Claims, 2 Drawing Sheets

FIGURE 1a

```
                                                                                                              - = continuity of aminoacid sequence
                                                                                                              p = phosphate group on tyrosine
Hepreceptor1        308                    domain A
Aminoacid           A R E E K H Q K Q L E R Q Q L E T E K K - R R E T V E R E K E Q M
Side chain charge   + - - - + - - + - - + - - + + - - + + + - - + + + - - - + -

Side chain charge       - + -   - + - -   + - +   + + -   + - - - + - + - -   + - + - +
Aminoacid           Q L A R Q I Q E S L E R E A K K T K E E Y D Q L R L M L E E K E R M
                    373                         domain B
```

FIGURE 1b

```
Hepreceptor1                                                                      K K - R R E T V E R E
Inverted sequence                                                                 + + - + + - - + - +
Side chain charge       - + -   - + - -   + - +   + + -   + - - - + - + - -   + - + - +     - + + +   - - + + + - - - + - + + - +   - + + + - + - -   + + - - - + -
aminoacid           Q L A R Q I Q E S L E R E A K K T K E E Y D Q L R L M L E E K E R M M Q E K E R E V T E R R - K K E T E L Q Q R E L Q K Q H K E E R A
                    373                         domain B                p             Hinge                            domain A                                    308
```

FIGURE 1c

```
Hepreceptor2        308                    domain A                                                     Hinge                               domain B                                                  373
Aminoacid           A R E E K H Q K Q L E R Q Q L E T E K K - R R E T V E R E K E Q M M R E K E E L M L R L Q D Y E E K T K K A E R E L S E Q I Q R A L Q
Side chain charge   + - - - + - - + - - + - - + + - - + + + - - + + + - - - + -       + - - + + - - - - + - - - - + +     - + + - - + + - - + + - - - +     - +

Side chain charge       - + -   - + - -   + - +   + + -   + - - - + - + - -   + - + - +     - + + +   - - + + + - - - + - + + - +   - + + + - + - -   + + - - - + -
aminoacid           Q L A R Q I Q E S L E R E A K K T K E E Y D Q L R L M L E E K E R M M Q E K E R E V T E R R - K K E T E L Q Q R E L Q K Q H K E E R A
Hepreceptor1        373                         domain B                p             Hinge                            domain A                                    308
Inverted sequence
```

REGULATORY/UNFOLDING PEPTIDES OF EZRIN

This application is a 371 of PCT/GB00/03566 filed Sep. 15, 2000, which claims the priority of United Kingdom Application No. 992188.0, filed Sep. 17, 1999.

BACKGROUND TO THE INVENTION

The field of the present invention relates to the treatment of infectious disease and cancer by inducing disease fighting immune responses. The growing problem of new strains of pathogenic bacteria resistant to antibiotics, the limited range of compounds effective against chronic viral and fungal infections and shortage of effective anti-cancer treatments demonstrates the need for compounds that can enhance the host defence against these medical problems. This invention relates to novel charged molecules which stimulate immune responses by binding to the Hepreceptor, a novel active site in human ezrin which I have discovered. The preferred charged molecules are novel peptides with sequences identical to the Hepreceptor in human ezrin.

Ezrin is a member of the ERM (ezrin-radixin-moesin) family of proteins which play structural and regulatory roles in a wide range of cell types. There is considerable evidence to indicate that ezrin regulates the structure of the cortical cytoskeleton to control cell surface topography. Ezrin adopts two main conformations: 1) a soluble folded form which is found in the cytoplasm and. 2) an unfolded and elongated form which is found attached to the cytoplasmic surface of the cell membrane particularly in conduction with microvilli and other activation related structures. The N terminal domain of the protein is attached to the cytoplasmic surface of the membrane while the C terminal part binds to the actin cytoskeleton. Ezrin is a tyrosine kinase substrate in T cells and is also tyrosine phosphorylated as a result of Epidermal Growth Factor (EGF) stimulation of the EGF receptor. The N terminal domain of ezrin in its extended conformation binds to the cytoplasmic tail of CD44 in the presence of $PIP_2$. Ezrin also may bind to the cytoplasmic tail of ICAM-2. Ezrin is very sensitive to regulatory proteases such as calpain and is rapidly turned over during cell activation.

Anthony Bretscher, David Reczek and Mark Berryman (1997).

"Ezrin: a protein requiring conformational activation to link microfilaments to the plasma membrane in the assembly of cell surface structures" *Journal of Cell Science* 110: 3011–3018.

Detailed analysis of the secondary structure of ezrin shows that there are three main structural domains: an N terminal domain from amino acids 1 to 300, a highly charged alpha domain from amino acids 300 to 470 and C terminal domain from amino acids 470 to 585. Structural modelling suggests that the alpha domain is folded into two anti-parallel helices in the soluble globular form of ezrin although the location of the hinge has not been identified. In the model of the extended phosphorylated form, ezrin is attached to the inner surface of the cell membrane by the N terminal domain, the alpha domains of two ezrin molecules are paired into anti-parallel dimers and located below the cell surface membrane. In this extended form, ezrin is tyrosine phosphorylated at tyrosine 353 (Yp 353).

Ossi Turunen, Markku Sainio, Juha Jaaskelainen. Olli Carpen, Antti Vaheri (1998) "Structure-Function relationships in the ezrin family and the effect of rumor-associated point mutations in neurofibromatosis 2 protein" *Biochimica el Biophysica Acta* 1387: 1–16.

I disclosed in U.S. Pat. No. 5,773,573 that the fourteen amino acid peptide HEP1, (amino acid sequence of TEKKRRETEREKE, SEQ ID 28, identical to amino acids 324 –337 of human ezrin) which has a 70% identity to the C terminus of gp120 could inhibit HIV replication in vivo in man. At the time I believed that the observed anti-HIV effect of peptide HEP1 was due to the orally administered HEP1 inducing

TABLE 1

Amino acids, three letter code, one letter code and side chain charges
CHARGES ON AMINO ACID SIDE CHAINS AT PHYSIOLOGICAL pH

| Amino acid | Three letter code | One letter code | Charge | Symbol |
|---|---|---|---|---|
| Glycine | Gly | G | NONE | |
| Alanine | Ala | A | NONE | |
| Valine | Val | V | NONE | |
| Isoleucine | Ile | I | NONE | |
| Leucine | Leu | L | NONE | |
| Serine | Ser | S | NONE | |
| Threonine | Thr | T | NONE | |
| Aspartic acid | Asp | D | NEGATIVE | -- |
| Glutamic acid | Glu | E | NEGATIVE | -- |
| Phosphotyrosine | Tyr(P) | Yp | NEGATIVE | -- |
| Asparagine | Asn | N | WEAK NEGATIVE | - |
| Glutamine | Gln | Q | WEAK NEGATIVE | - |
| Lysine | Lys | K | POSITIVE | + |
| Arginine | Arg | R | POSITIVE | + |
| Histidine | His | H | WEAK POSITIVE | + |
| Proline | Pro | P | NONE | |
| Tryptophan | Trp | W | NONE | |
| Phenylalanine | Phe | F | NONE | |
| Tyrosine | Tyr | Y | NONE | |
| Methionine | Met | M | NONE | |
| Cysteine | Cys | C | NONE | |

BRIEF DESCRIPTION OF THE DRAWINGS

FIGS. 1a, 1b and 1c are diagrams of the alignments of the primary amino acid sequences of:
  a) the folded anti-parallel associated helices of the Hepreceptor in soluble ezrin.
  b) the unfolded helix of the Hepreceptor in membrane associated ezrin with an example of a peptide ligand.
  c) two unfolded Hepreceptor forming a dimer of anti-parallel associated helices during an interaction between two cells.

BRIEF DESCRIPTION OF THE SEQUENCES

Figure 2:
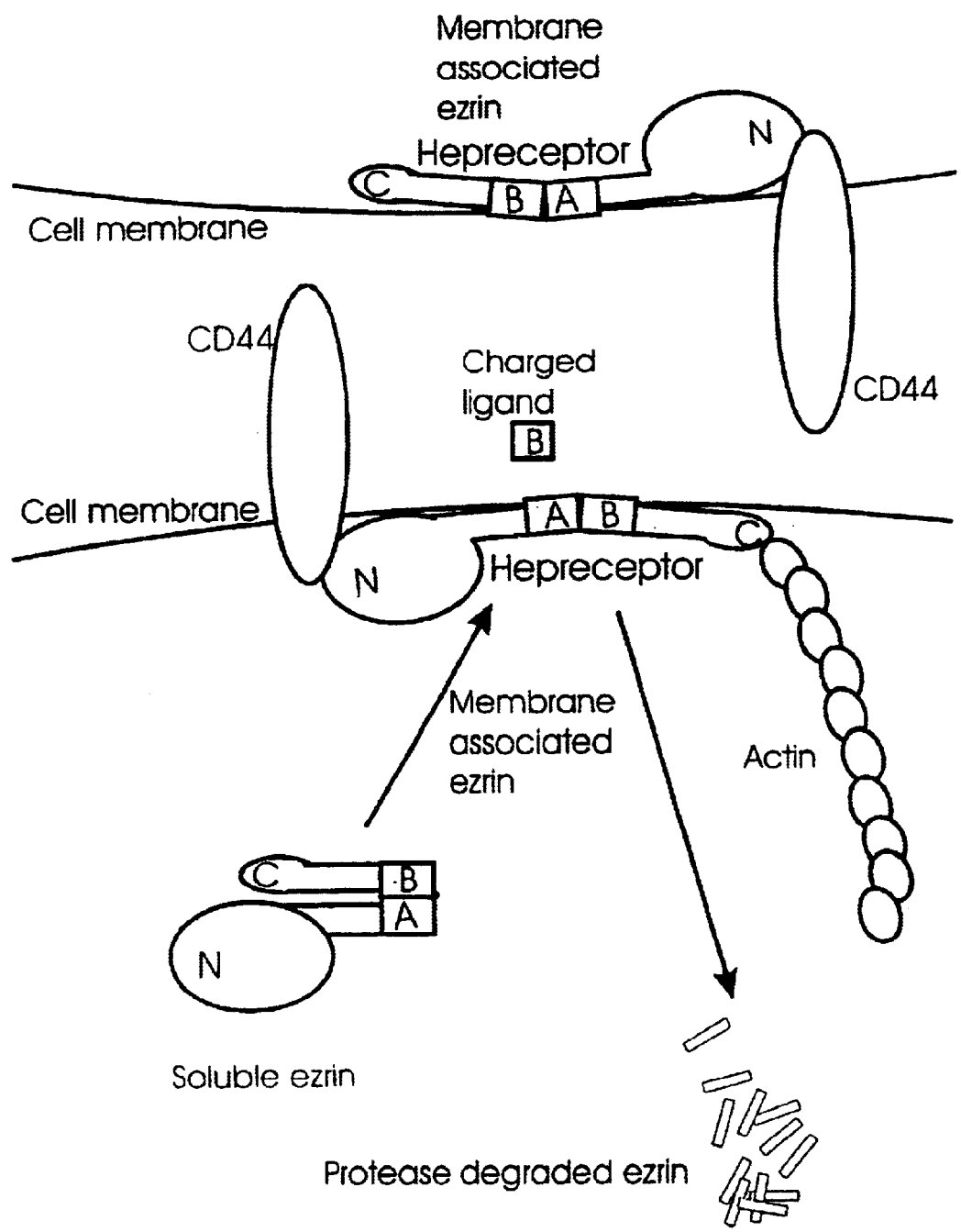
FIG. 2 is an illustration of the relationship between the Hepreceptor on ezrin, its ligands, cell membranes, cell surface receptors and cytoskeletal components.

SEQ ID 1 is an amino acid sequence of a peptide according to the present invention.
SEQ ID 2 is an amino acid sequence of a peptide according to the present invention.
SEQ ID 3 is an amino acid sequence of a peptide according to the present invention.
SEQ ID 4 is an amino acid sequence of a peptide according to the present invention.
SEQ ID 5 is an amino acid sequence of a peptide according to the present invention.
SEQ ID 6 is an amino acid sequence of a peptide according to the present invention.
SEQ ID 7 is an amino acid sequence of a peptide according to the present invention.

SEQ ID 8 is an amino acid sequence of a peptide according to the present invention.
SEQ ID 9 is an amino acid sequence of a peptide according to the present invention.
SEQ ID 10 is an amino acid sequence of a peptide according to the present invention.
SEQ ID 11 is an amino acid sequence of a peptide according to the present invention.
SEQ ID 12 is an amino acid sequence of a peptide according to the present invention.
SEQ ID 13 is an amino acid sequence of a peptide according to the present invention.
SEQ ID 14 is an amino acid sequence of a peptide according to the present invention.
SEQ ID 15 is an amino acid sequence of a peptide according to the present invention.
SEQ ID 16 is an amino acid sequence of a peptide according to the present invention
SEQ ID 17 is an amino acid sequence of a peptide according to the present invention.
SEQ ID 18 is an amino acid sequence of a peptide according to the present invention.
SEQ ID 19 is an amino acid sequence of a peptide according to the present invention.
SEQ ID 20 is an amino acid sequence of a peptide according to the present invention.
SEQ ID 21 is an amino acid sequence of a peptide according to the present invention.
SEQ ID 22 is an amino acid sequence of a peptide according to the present invention.
SEQ ID 23 is an amino acid sequence of a peptide according to the present invention.
SEQ ID 24 is an amino acid sequence of a peptide according to the present invention.
SEQ ID 25 is an amino acid sequence of a peptide according to the present invention.
SEQ ID 26 is an amino acid sequence of a peptide according to the present invention.
SEQ ID 27 is an amino acid sequence of a peptide according to the present invention.
SEQ ID 28 is an amino acid sequence of a peptide according to the present invention.

DETAILED DESCRIPTION OF THE INVENTION

The soluble conformation of ezrin found in the cytoplasm comprises of two adjacent alpha helical domains which are folded together at a hinge region (M339–M340) into two anti-parallel helices stabilised by complimentary side chain charges of the primary amino acid sequence. It is the subject of this invention that the positively and negatively charged side chains of the amino acid sequence of Hepreceptor Domain A are complementary to the positively and negatively charged side chains of the amino acid sequence of the Hepreceptor Domain B. In the activated open conformation of ezrin, the interaction of the Domain A and Domain B of the Hepreceptors of two different ezrin molecules allows the formation of anti-parallel dimers. In addition to the antiparallel dimers of ezrin which form below the cell surface, I have determined that these dimers can form between a Hepreceptor exposed on the surface on one cell with a Hepreceptor exposed on the surface of another cell. When the two Hepreceptors make contact during close association of two cell surfaces an activation signal is initiated in both cells (FIG. 2). Any charged molecule that partially mimics the interaction between the side chains charges of Domain A and Domain B of the Hepreceptors will give rise to a medically useful biological response.

Hepreceptor-Domain A (amino acid numbers 308–339 of human ezrin), comprises of the following 32 amino acid sequence.

(The sequence are listed using the single letter code for ch amino acid written from the N terminus to the C terminus of the polypeptide Yp represents the form of phosphotyrosine found in vivo).

SEQ ID 1 AREEKHQKQLERQQLETEKKRRE-TVEREKEQM

In U.S. Pat. No. 5,773,573, I disclosed the anti-HIV activity of peptide HEP1 (SEQ ID 28) which I have now discovered has a sequence identical to part of Hepreceptor-Domain A (spanning amino acids 324–337 of the human ezrin sequence). In the above patent I made the assumption that anti-HIV activity was due to the induction of immunological tolerance to autoreactive immune responses induced by the C terminus of HIV gp120. I can now disclose that the anti-HIV activity of HEP1 is due to its binding to Hepreceptor Domain B and the induction of a novel immune response. It is a subject of this invention that there are novel peptides derived from the Hepreceptor of ezrin with significantly superior activity to HEP1.

Hepreceptor-Domain B (amino acid numbers 340–373 of human ezrin), comprises of the following 34 amino acid sequence (Tyrosine 353 [Y] may be phosphorylated to phosphotyrosine [Yp] in the membrane associated conformation of ezrin):

SEQ ID 2 MREKEELMLRLQDY(p)EEKTKKA-ERELSEQIQRALQ

I have determined that Domain B of the Hepreceptor is the site on ezrin to which HIV gp120 binds during infection of the brain. (HIV gp120 binds to Hepreceptor Domain B using its charged C terminal amino acids which have a 70% identity to part of Hepreceptor Domain A). Novel charged molecules which bind to the Hepreceptor may be useful in treating HIV related dementia.

Claudia Hecker, Christoph Weise, Jurgen Schneider-Schaulies, Harvey Holmes, Volker ter Meulen (1997) "Specific binding of HIV-1 envelope protein gp120 to the structural membrane proteins ezrin and moesin." Virus Research 49 215–223.

I have demonstrated (EXAMPLE 1A) that Hepreceptor peptides have significant adjuvant activity and this is demonstrated by enhancing the IgG antibody response to Ovalbumin in mice using HEP1, Rupe312, Rupe1014. Rupe1024 and Rupe2032. I have also demonstrated (EXAMPLE 1B) the activity of Hepreceptor peptides in enhancing the antibody-dependent cytotoxic response in Thymus to Sheep Red Blood Cells (SRBC) in mice using HEP1. Rupe312, Rupe15, Rupe1014, Rupe1024 and Rupe2032.

(Rupe312 SEQ ID 8:KKRRETVERE and Rupe15 SEQ ID 3, TEKKR and Rupe1014 SEQ ID 16: EREKE and Rupe1024 SEQ ID 17: EREKEQMMREKEEL and Rupe2032 SEQ ID 19: KEELMLRLQDYEE and HEP1 SEQ ID 28: TEKKRRETVEREKE).

I have demonstrated (EXAMPLE 2) that hepreceptor peptides have significant anti-tumour activity and this is demonstrated by Hepreceptor peptides reducing the growth rate of fast growing transplanted sarcomas and slower growing transplanted cervical cancer in mice using Rupe312 and Rupe414.

(Rupe312 SEQ ID 8:KKRRETVERE and Rupe414 SEQ ID 13: KRRETVEREKE).

I have demonstrated (EXAMPLE 3) that HEP1 therapy (10 mg per day orally either for thirty days or ninety days) in 21 HIV infected patients induces immune responses which leads to clinical improvement over the following six months after therapy, as measured by an increasing CD4 T lymphocyte population and declining opportunistic infections, declining HIV infectivity and declining CD38.CD8 population of T lymphocytes (an established prognostic marker of the progression to AIDS).

M Levancher, F Hulstaert, S. Tallet, S Ullery, J J Pocidalo, B A Bach (1992).

"The significance of activation markers on CD8 lymphocytes in human immunodeficiency syndrome: staging and prognostic value" *Clinical Experimental Immunology* 90 376–382.

A mean increase in the level of expression of CD44 and MHC Class I on T lymphocytes over six months was observed which appears to also correlate with the clinical improvement. No toxicity was detected with the administration of HEP1. Increases of MHC Class I expression and CD44 expression are associated with increases in memory T cells and Class I restricted cell mediated immunity.

Stephan Oehen and Karin Brduscha-Riem (1998).

"Differentiation of Naive CTL to Effector and Memory CTL: Correlation of Effector Function with Phenotype and Cell Division" *The Journal of Immunology* 161 5338–5346.

The results of this trial demonstrates that a peptide or other charged molecule which mimics all or part of the Hepreceptor can give rise to an activation signal that eventually leads to a change in the homoeostasis of the immune system and long term up regulation of cell mediated and humoral immunity. I have also demonstrated that acute and chronic *candida* infection in women can be treated and cured by the immune response arising from Hepreceptor stimulation (EXAMPLE 4). I have demonstrated that peptides derived from the Hepreceptor can activate monocytes and macrophages in mice both in vitro and in vivo, which leads to a protective immune response. (EXAMPLE 5). Peptides of this invention have a significantly higher activity than HEP1. Hepreceptor stimulation also leads to the activation of human peripheral blood mononuclear cells which was demonstrated by measuring the incorporation of radioactive tritiated thymidine into DNA of the growing cells. Novel peptides, Rupe312 and Rupe414 derived form Hepreceptor Domain A had a ten fold higher activity than HEP1. (EXAMPLE 6).

(Rupe312 SEQ ID 8:KKRRETVERE and Rupe414 SEQ ID 13: KRRETVEREKE).

I also discovered that a 24 hour incubation of human White Blood Corpuscles (WBC) with peptides derived from the Hepreceptor results in a fall in MHC Class I cell surface expression, probably due to cell activation and receptor internalisation, and an increase in the total population of macrophages expressing MHC Class I. This is consistent with the long term increase in the population cells expressing MHC Class I seen in HIV patients during the six months following HEP1 therapy. In this assay system Rupe312 and Rupe414 had significantly higher activity than HEP1 (EXAMPLE 7).

(Rupe312 SEQ ID 8:KKRRETVERE and Rupe414 SEQ ID 13: KRRETVEREKE).

I have demonstrated (EXAMPLE 8) that hepreceptor peptides have significant suppressive effect on the expression of IL-8. The inhibition of IL-8 may play a role in the selective activity of hepreceptor peptides in activating monocytes/macrophages (Rupe312 SEQ ID 8:KKRRETVERE).

I have demonstrated (EXAMPLE 9) that very low dose Hepreceptor peptides (1–100 nanograms/mouse) protect mice from acute infection by *Salmonella* tryphimurium (Rupe15 SEQ ID 3: TEKKR and Rupe1024 SEQ ID 17: EREKEQMMREKEEL and HEP1 SEQ ID 28: TEKKRRETVEREKE).

I have demonstrated (EXAMPLE 10) that very low dose Hepreceptor peptides (1–1000 nanograms/mouse) enhance survival time in a mouse lethal herpes virus infection model. (HEP1 SEQ ID 28: TEKKRRETVEREKE).

This invention describes charged molecules which specifically bind to the Hepreceptor. I have designed three groups of novel charged peptides which have sequences identical to the amino acid sequences of the complementary domains of the Hepreceptor and which either bind to Hepreceptor Domain B (SEQ ID 3–SEQ ID 16), or to both Domain A and B (SEQ ID 17), or which bind to Domain A (SEQ ID 18–SEQ ID 27). The peptides which are a subject of this invention probably bind to cell surface exposed Hepreceptors and stabilise the unfolded conformation of ezrin and induce immuno-modulatory effects. The preferred peptides are between five and thirteen amino acids in length and the preferred sequences are as follows.

Hepreceptor Domain B binding peptides:
SEQ ID 3
Rupe15: TEKKR
SEQ ID 4
Rupe19: TEKKRRETV
SEQ ID 5
Rupe111: TEKKRRETVER
SEQ ID 6
Rupe37: KKRRE
SEQ ID 7
Rupe310: KKPRRETVE
SEQ ID 8
Rupe312: KKRRETVERE
SEQ ID 9
Rupe313): KKRRETVEREK
SEQ ID 10
Rupe314: KKRRETVEREKE
SEQ ID 11
Rupe411: KRRETVER
SEQ ID 12
Rupe413: KRRETVEREK
SEQ ID 13
Rupe414: KRRETVEREKE
SEQ ID 14
Rupe59: RRETV
SEQ ID 15
Rupe614: RETVEREKE
SEQ ID 16
Rupe1014: EREKE
Hepreceptor Domain A and Domain B binding peptide:
SEQ ID 17
Rupe1024 EREKEQMMREKEEL
Hepreceptor Domain A binding peptide:
SEQ ID 18
Rupe2024; KEELM
SEQ ID 19
Rupe2032: KEELMLRLQDYEE
SEQ ID 20
Rupe2032p: KEELMLRLQDYpEE
SEQ ID 21
Rupe2132: EELMLRLQDYEE
SEQ ID 22
Rupe2132p: EELMLRLQDYpEE
SEQ ID 23
Rupe2232: ELMLRLQDYEE
SEQ ID 24
Rupe2232p: ELMLRLQDYpEE
SEQ ID 25

Rupe2428: MLRLQ
SEQ ID 26
Rupe2832: QDYEE
SEQ ID 27
Rupe2832: QDYpEE

Other peptides or other charged molecules which bind to Domain A or Domain B or bridge Domain A and Domain B of the Hepreceptor are likely to be biologically active. These peptides or other charged molecules can be administered orally and by other routes for the treatment of various infectious diseases and cancer.

How to Make

Peptides used in this invention may be synthesised for example, using a solid phase method using either Boc or Fmoc chemistry or any other practical route for peptide synthesis known to those skilled in the art of peptide synthesis.

Stepwise solid phase synthesis with Boc-amino acids can be performed based on the method of Merrifield; (Journal of American Chemical Society 85 2149–2154). The following compounds can be used (Novabiochem resin: Boc-Glu (OBzl)-PAM, Amino acids: Boc-Lys (2Cl—Z—)OH, Boc-Glu(OBzl)OH, Boc-Arg(Tos)OH, Boc-Val-OH. Boc-Thr (Bzl)—OH, Solvents: DMF (Rathburn), Dichloromethane (BDH), Ethylacetate (BDH). Reagents: HBTU (Phase Separations Ltd), p-Cresol (Lanchester) TFA (Halocarbon Products Corporation) HF (BOC) DIEA (Fluka). Recommended reactive side chain protecting groups for Boc-amino acids are:, Arg (Tos), Asn (Xan), Asp (OcHxl), Glu (OcHxl) Gln (Xan) or Gln, His (DNP), Lys (ClZ). Serine (Bzl) Tyr (BrZ) Trp (CHO). The abbreviations have the following meanings: DCC=Dicyclohexylcarbodiimide. DIC=Diisopropylcarbodiimide. DCM=Dichloromethane, DMF=Dimethylformamide, TFA=Trifluoracetic acid, Boc=t-Butyloxycarbonyl, HOBT=Hydroxybenzotriazole, DIEA=Diisopropylethylamine, DCU=Dicyclohexylurea.

For example, boc synthesis of a peptide of this invention could be performed as follows: HBTU activation/in situ neutralization on 0.5 mmol scale uses 0.5 mmol of resin and a three fold excess of activated Boc amino acid. Boc amino acid and activating reagent (HBTU) should be used in equimolar quantities ie 2 mmol each in this case equals a 3×excess. DIEA is used to both neutralise the resin for coupling and to activate the Boc-amino acid. (Hence 2.5 mmol is used. 1 equivalent Boc-aa and 1 equivalent resin). Reagents: 0.5M HBTU in DMF (MW=379, 0.5M=18.95 g in 100 ml, note it is not light stable) requires 2 mmol=4 ml and 2.5 mmol DIEA=0.46 ml (MW=129, d=0.742). Activation of aminoacids: Boc-amino acid should be activated only immediately prior to addition to the resin, especially in the case of Arg (Tos). For all Boc amino acids: weigh 2 mmol Boc amino acid into a 20 ml glass sample bottle. Add 4 ml 10.5M HBTU solution and shake to dissolve solid. Add 0.46 ml DIEA and mix (some colour change may be observed). Method: wash resin with DMF, remove Boc-protecting group with 100% TFA—Shake twice for 1 minute draining in between, drain, flow wash with DMF for 1 minute, drain, add activated amino acid solution, shake for 10 minutes, then take sample and perform the ninhydrin test to determin coupling efficiency. On completion of the synthesis flow wash with DMF, then DCM and dry. The synthesis of the first and every subsequent level of peptide construction is achieved using a three fold excess of HBTU activated Boc-amino acids in DMF. In all couplings, the coupling efficiency should be more than 99% as indicated by quantative ninhydrin testing. Deprotection of the N-termini is performed in 100% TFA. The resin peptide is carefully flow-washed before and after the deprotection. After the last coupling and removal of the Boc-protection, the peptide resin is washed with dichloromethane and dried by air. The peptide is removed from the resin support by the high HF method (2 g resin peptide, 2 g cresol, 20 ml HF, 1.5 h at −5° C.) to yield the crude peptide which is precipitated with ethylacetate (100 ml) and redissolved in 6M guanidine HCL-0.1M TRIS solution (20 ml).

The peptide can be purified as follows using an analytical HPLC separation on a Vydac $C_{18}$ 5 RAC column. HPLC grade acetonitrile (aldrich) and water is filtered through a membrane filter and degassed with helium flow prior to use. Analytical separation achieved with a solvent gradient beginning with 0% acetonitrile, increasing constantly to 60% acetonitrile at 20 minutes, staying at this concentration for twenty minutes and decreasing steadily to 0% acetonitrile for 10 minutes at a constant flow of 1.2 ml per minute. Preparative separation of peptide achieved on a TSK-GEL preparative $C_{18}$ column. Separation is achieved with a solvent gradient beginning with 0% acetonitrile, increasing constantly to 18% acetonitrile at 60 minutes, then 60% acetonitrile for 80 minutes, staying at this concentration for 30 minutes at a constant flow of 8 ml per minute. The gradient can be controlled by two microprocessor controlled Gilson 302 single piston pumps. Compounds can be detected with a Waters 486 Tunable Absorbance Detector at 214 nm and analytical chromatographs recorded with an HP laserjet 5L. A Holochrome UV-VIS detector 220 nm for preparative chromatographs can be recorded with an LKB 2210 single channel recorder. Capillary Electorphoresis quality control can be carried out using Waters Quanta 4000 equipment using a phosphate buffer (75 microM) pH2.5 run at 15 kV, sample time 20 seconds, loaded by hydostatic injection on 60 cm column, run time 12 minutes. The yield for 1 g 0.46 mmol resin synthesis should be about 250 mg pure peptide Alternative solution synthesis methods may also be used to produce larger quantities of the peptides of this invention. Protected trimer fragments can be obtained using stepwise synthesis by the active esters method known to those skilled in the art of peptide synthesis. The fragments are then assembled using DCC/HOBT after removal of relevant C and N terminal protective groups. After removal of all protective groups the crude peptide is partially purified on SP-Sephadex-C25 ion exchange chromatography followed by preparative HPLC then lyophilised.

How to Use 0.01 to 1000 mg of lyophilised peptide may be dissolved in 1–10 ml distilled water and administered orally or vaginally. 0.01 to 1000 mg may be formulated in to a pill or capsule or suppository with carriers used commonly by those skilled in the art of pill or capsule or suppository manufacture and administered orally or vaginally or anally. A filter sterilized solution of between 0.001 and 100 milligrams of peptide in distilled water may be injected subcutaneously or intravenously or intramuscularly.

The following Examples serve to illustrate the invention only, and should not be construed as limiting it in any way.

EXAMPLE 1A

Adjuvant Activity of Hepreceptor Peptides Enhancing the IgG Serum Antibody Response to Ovalbumin in Mice The IgG response in mice two weeks after an injection of 50 micrograms of Ovalbumin plus various concentrations of different hepreceptor peptides was determined. IgG response was measured by Optical Density (OD) of a 1 to 100 dilution of mouse sera in the presence of Ovalbumin.

Results
IgG response recorded as OD

| Peptide code | Control 0 | IP injection in micrograms per mouse | | | | Peptide sequence |
|---|---|---|---|---|---|---|
| | | 0.01 | 0.1 | 1 | 10 | |
| HEP1 | 0.69 | 0.45 | 0.44 | 0.56 | 0.57 | TEKKRRETVEREKE |
| Rupe312 | 0.69 | 0.68 | 0.88 | 0.55 | 0.44 | KKRRETVERE |
| Rupe1014 | 0.127 | 0.232 | 0.231 | 0.477 | 0.508 | EREKE |
| Rupe1024 | 0.152 | 0.250 | 0.262 | 0.489 | 0.445 | EREKEQMMREKEEL |
| Rupe2032 | 0.127 | 0.509 | 0.606 | 0.327 | 0.203 | KEELMLRLQDYEE |

IgG response recorded as OD then data rebased relative to 100 for each control

| Peptide code | Control 0 | IP injection in micrograms per mouse | | | | Peptide sequence |
|---|---|---|---|---|---|---|
| | | 0.01 | 0.1 | 1 | 10 | |
| HEP1 | 100 | 65 | 64 | 81 | 83 | TEKKRRETVEREKE |
| Rupe312 | 100 | 99 | 128 | 80 | 64 | KKRRETVERE |
| Rupe1014 | 100 | 183 | 182 | 376 | 400 | EREKE |
| Rupe1024 | 100 | 164 | 172 | 322 | 293 | EREKEQMMREKEEL |
| Rupe2032 | 100 | 401 | 477 | 257 | 160 | KEELMLRLQDYEE |

Conclusion

All the hepreceptor peptides with the exception of HEP1 show adjuvant activity but with different optimal concentrations.

EXAMPLE 1B

Activity of Hepreceptor Peptides Enhancing the Antibody-Dependent Cytotoxic Response in Thymus to Sheep Red Blood Cells (SRBC) in Mice The influence of Hepreceptor peptides on the activation of antibody forming cells against sheep erythrocytes (SRBC) in Mice (CBA-C57B1 Fi hybrids. 2 months old, weight 18–22 grams) was determined. Mice were first injected intraperitoneally using either 0.5 ml sterile saline as a control or Hepreceptor peptides in the same volume of saline. 30 minutes after the injection of Hepreceptor peptides, a cell suspension containing 5 million SRBC was administered intraperitoneally to each mouse. Four days after the immunisation, the mice were killed by cervical dislocation and the spleens were obtained aseptically. Each spleen was homogenised in 2 ml of Medium 199, then 100 microliters of this suspension was put into 1 ml of prepared agarose in Medium 199 (stored in water bath at 48° C.), SRBC suspension was added, resulting in a final concentration of 1% agarose. The Im1 of agarose-cell mixture was agitated then transferred to petri dish to set. When the agarose became solid, the petri dish was incubated for 1 hour at 37° C. then 0.5 ml of 1-in-20 diluted guinea pig serum in Medium 199 was added on top of agarose gel as a source of complement. The incubation was continued for another 1 hour. The dishes were then visualised using an 8×binocular microscope and the number of plaques counted (each plaque equivalent to one antibody secreting mouse spleen cell). The results were expressed both as the number of antibody secreting cells per one million nucleated spleen cells and the number of antibody secreting cells per whole spleen. As no mitogenic effect was observed (Hepreceptor peptide administration resulted in normal sized mouse spleens), these two calculations gave similar results.

Averaged data (from thirty mice per data point) of the number of antibody forming cells per one million nucleated spleen cells. The data was re-based relative to 100 for each control group.

| Peptide code | Control 0 | IP injection in micrograms per mouse | | Peptide sequence |
|---|---|---|---|---|
| | | 1 | 10 | |
| HEP1 | 100 | 192 | 203 | TEKKRRETVEREKE |
| Rupe312 | 100 | 317 | 267 | KKRRETVERE |
| Rupe15 | 100 | 255 | 134 | TEKKR |
| Rupe1014 | 100 | 202 | 325 | EREKE |
| Rupe1024 | 100 | 401 | 397 | EREKEQMMREKEEL |
| Rupe2032 | 100 | 236 | 232 | KEELMLRLQDYEE |

(Rupe312 SEQ ID 8: KKRRETVERE and Rupe15 SEQ ID 3: TEKKR and Rupe1014 SEQ ID 16: EREKE and Rupe1024 SEQ ID 17: EREKEQMMREKEEL and Rupe2032 SEQ ID 19: KEELMLRLQDYEE and HEP1 SEQ ID 28: TEKKRRETVEREKE)

Conclusion

All the Hepreceptor peptides enhance the antibody-dependent cytotoxic response in thymus but with different optimal concentrations.

EXAMPLE 2

Anticancer Activity of Hepreceptor Peptides on the Growth of Transplanted Sarcoma of the Uterus SM-322 and on Cancer of the Uterine Cervix CUS-5 Performed in CBA Mice Using Rupe312 and Rupe414 as Examples Materials and Methods Transplanted mouse sarcoma SM-322 model (endothelial tumour).

Primary tumours of the uterus were induced in female mice using 1.2 dimethylhydrazine. A few primary tumours were transplanted into syngeneic mice.

The first visible nodules started to appear at the point of transplation after 4 days. The life expectancy of the mice with transplanted tumours was 22–24 days.

Transplanted mouse cervical cancer model CUC-5 (epithelial tumour)

Primary tumours were induced in female mice using methylcholantrene. A few primary turnouts were then auto-transplanted into the uterine cervix. The life expectancy of mice with transplanted tumours was 43 days.

CBA Mice

CBA female mice weighed 21.4=/−1.2 g. and were 2–3 months old. The tumours were introduced as a 0.5 ml of tumour suspension (1 g tumour per 10 ml of Igla medium) and ten mice used in each treatment group.

Peptide Preparation and Administration

Lyophylised peptide were dissolved in sterile physiological saline immediately before use in three concentrations. 0.5 ml of solution was injected twice weekly into the peritoneum of the mice for the duration of the experiment. Three different concentrations of peptide were used leading to three final doses per injection per mouse of 10, 1.0 and 0.1 micrograms.

Results

The average percent decrease of tumour volume relative to the control group was recorded at three time points. The longevity of the mice in the treatment groups and control groups was compared and the histology of the tumours between control and treatment groups was compared.

Transplanted mouse sarcoma model SM-322

|         |              | Percent decrease in tumour volume relative to control | | | Days of life |
|---------|--------------|--------|--------|--------|----------|
| Peptide | Microg/mouse | Day 8  | Day 12 | Day 15 | expectancy |
| Rupe312 | 10           | 63     | 54     | 27     | 12–27 |
|         | 1            | 67     | 32     | 38     | 12–19 |
|         | 0.1          | 61     | 34     | 59     | 12–22 |
| Rupe414 | 10           | 65     | 43     | 43     | 13–20 |
|         | 1            | 68     | 28     | 43     | 12–20 |
|         | 0.1          | 68     | 39     | 22     | 12–19 |
|         |              | Volume Day 8 | Volume Day 12 | Volume Day 15 | |
| Control |              | 1.49   | 11.2   | 17.7   | 12–16 |

Transplanted mouse cervical cancer model CUC-5

|         |              | Percent decrease in tumour volume relative to control | | | Days of life |
|---------|--------------|--------|--------|--------|----------|
| Peptide | Microg/mouse | Day 8  | Day 12 | Day 19 | expectancy |
| Rupe312 | 10           | 50     | 25     | 49     | 48–76 |
|         | 1            | 50     | 26     | 49     | 47–76 |
|         | 0.1          | 50     | 18     | 45     | 42–76 |
| Rupe414 | 10           | 50     | 16     | 48     | 36–76 |
|         | 1            | 50     | 16     | 43     | 36–76 |
|         | 0.1          | 50     | 18     | 57     | 47–76 |
|         |              | Volume Day 5 | Volume Day 12 | Volume Day 19 | |
| Control |              | 0.06   | 0.68   | 1.56   | 47–76 |

(Rupe312 SEQ ID 8: KKRRETVERE and Rupe414 SEQ ID 13: KRRETVEREKE)

Conclusion

Hepreceptor peptides Rupe312 and Rupe414 reduce the growth rate of fast growing transplanted sarcomas leading to a slight (3–18%) increase in life expectancy.

Hepreceptor peptides Rupe312 and Rupe414 reduce the growth rate of slower growing transplanted cervical cancer but no significant increase (or decrease) in life expectancy was detected.

Hepreceptor peptides Rupe312 and Rupe414 induced a non bleeding ulcerous destruction of the centre of tumours in both models which consistently lead to smaller tumour volumes.

EXAMPLE 3

HEP1, a Hepreceptor Peptide, Administered Orally (10 mg per Day Either for Thirty Days or Ninety Days) to 21 HIV Infected Patients Led to Clinical Improvement. The Success of this Study Demonstrates Generally the Utility and Reduction to Practice of Peptides Derived from the Hepreceptor This study was performed with pharmaceutical grade HEP1, a peptide which has an identical sequence to part of Domain A of the Hepreceptor. HIV-infected volunteers were recruited for the study at the Institute of Immunology, Moscow under the guidance of Professor Ravshan Ataullakhanov. The pharmaceutical grade HEP1 passed an extensive range of animal (rat and rabbit) toxicology and pre-clinical testing before the trial commenced, which demonstrated the safety of the compound. (Preliminary evaluation of toxicity-negative, Effect of 1000× therapeutic dose-negative, Local Irritation-negative, Influence on CNS and HVS-negative, Sub-acute toxicity-negative, Mutagenic effects-negative, Chronic toxicity-negative, Embryotoxicity-negative)

Study Plan

Patients were orally administered a solution of 10 mg of HEP1 in 2 ml sterile distilled water once a day in the morning before breakfast (the solution was prepared and stored is separate 10 mg lots at −20° C.). All patients were administered a coded placebo solution of distilled water for thirty days before treatment. A first group of 11 patients were administered HEP1 for 90 days and a second group of 10 patients were administered HEP1 for 30 days fifteen months later, after the data from the first group of patients had been analysed. During the treatment period the patients were requested to attend the clinic once a week, undergo a medical examination and give a blood sample for analysis. The patients were also requested to co-operate with post treatment monitoring and attend the clinic once a month for six months for further medical examinations and donations of blood samples. 21 out of 21 patients co-operated with monitoring during the treatment period and 14 out of 21 patients agreed to post treatment monitoring. The patients were not receiving any other anti-retroviral therapy during or one month before HEP1 treatment.

Patients

Patients were recruited from various clinics around Moscow and gave informed written consent to participate in the trial. They were identified as HIV infected by a positive ELISA assay, had depressed T cell counts and experiencing some clinical manifestation of HIV related illness. The patients were subsequently shown to have a range of CD4 cells per microliter between 17 and 801 and a range of serum HIV RNA (Roche Labs Amplicor quantitative PCR assay) from undetectable to 230,000 copies per ml.

Patient characteristics at start of trial

| ID Code | Sex    | Age | Est Period of infection | CD4 cells/ microL | HIV RNA Copies/ ml | opportunistic infections | other |
|---------|--------|-----|-------------------------|-------------------|--------------------|--------------------------|-------|
| P1      | male   | 45  | 8                       | 219               | 500                | severe                   |       |
| P2      | male   | 33  | 2                       | 192               | 10000              | severe                   |       |
| P3      | female | 45  | 6                       | 481               | 2000               | severe                   |       |
| P4      | female | 16  | 8                       | 237               | 43000              | severe                   |       |
| P5      | male   | 27  | 2                       | 123               | <400               | moderate                 | very sick |
| P6      | female | 23  | 1                       | 357               | 10000              | moderate                 | Herpes z |
| P7      | male   | 23  | 8                       | 139               | 94000              | very low                 | Herpes z |
| P8      | female | 38  | 10                      | 320               | 22000              | very low                 | Ovarian cyst |
| P9      | male   | 43  | 3                       | 17                | 10000              | severe                   |       |
| P10     | male   | 19  | 2                       | 155               | 21000              | severe                   | On oplates |
| P11     | male   | 35  | 3                       | 188               | <400               | severe                   | Active TB |
| P12     | male   | 32  | 8                       | 175               | 13000              | severe                   |       |
| P17     | male   | 25  | 1                       | 478               | 11000              | severe                   |       |
| P21     | female | 37  | 10                      | 98                | 11000              | severe                   |       |
| P63     | male   | 35  | 1                       | 651               | 4000               | severe                   |       |

-continued

Patient characteristics at start of trial

| ID Code | Sex | Age | Est Period of infection | CD4 cells/ microL | HIV RNA Copies/ ml | opportunistic infections | other |
|---|---|---|---|---|---|---|---|
| P67 | female | 31 | 7 | 124 | 230000 | severe | Very sick |
| P68 | female | 51 | 2 | 597 | <400 | severe | Very sick |
| P69 | male | 34 | 1 | 192 | 8000 | severe | Active TB |
| P72 | male | 33 | 1 | 534 | 25000 | severe | Active TB |
| P73 | male | 30 | 1 | 801 | <400 | severe | Active TB |
| P76 | female | 38 | 7 | 72 | 9000 | severe | |

General Observations

The patients reported no adverse reactions to HEP1, and 17 patients reported they felt generally better and gained at between 1.5 Kg and 4.5 Kg in weight while on HEP1 therapy (one patient also felt better during the placebo period).

Adverse Reactions

No adverse reactions were detected. Clinical assessments including ultrasound examinations and an extensive series of biochemical, haematological, immunological blood tests and urine tests were performed.

ment only 33% were severely infected. Before treatment. 33% of the patients had S aureus infection of the pharynx, after treatment only 19% were infected.

CD4 T Lymphocytes

The group eleven patients were treated, for three months with HEP1 experienced an average gain of T cell numbers of 9% by the end of treatment and 32% on average over the following six months after treatment. The group ten patients who were treated for one month with HEP1 experienced an average gain of T cell numbers of 3% by the end of treatment and 20% on average over the following six months after treatment. The continued improvement suggests that some positive immunological change had been induced in the patients.

HIV Infectivity Assay by TCID

Viral load was measured by mixing HIV infected Peripheral Blood Mononuclear Cells (PBMC) from the patient with uninfected donor PBMC in a ratio between sample cells to culture cells of 1/16 and culturing at 37° C. for fourteen days. Culture viral load was measured by an Innogenetics HIVp24 assay and the results were recorded in picograms of HIVp24 antigen per ml.

Three Month Treatment

| Patient | P1 | P2 | P3 | P4 | P5 | P6 | P7 | P8 | P9 | P10 | P11 |
|---|---|---|---|---|---|---|---|---|---|---|---|
| Infectivity in pg/ml p24max at start of trial | 1039 | 315 | na | 386 | 515 | 203 | 1113 | 369 | 1074 | na | 480 |
| re-based to 100 at start | 100 | 100 | 0 | 100 | 100 | 100 | 100 | 100 | 100 | 0 | 100 |
| Phase 0 average | | | | | | 130 | | | | | |
| Phase 1 average | 7 | 32 | 0 | 28 | 0 | 47 | 0 | 39 | | | |
| Phase 2 average | 21 | 218 | 198 | 129 | 251 | 70 | 217 | 40 | | | 835 |
| Phase 3 average | 0 | 61 | 0 | 85 | 0 | 48 | | 24 | | | |

One Month Treatment

| Patient | P12 | P17 | P21 | P63 | P67 | P68 | P69 | P72 | P73 | P76 |
|---|---|---|---|---|---|---|---|---|---|---|
| Infectivity in pg/ml p24max at start of trial | 465 | 0.3 | 3.1 | 2.9 | 6642 | 6.5 | 3.2 | 2 | 1 | 4.5 |
| re-based to 100 at start | 100 | 100 | 100 | 100 | 100 | 100 | 100 | 100 | 100 | 100 |
| Phase 0 average | 288 | | | | | | | 251 | | |
| Phase 1 average | 24 | 0 | | | 5 | | 29 | 0 | | 73 |
| Phase 2 average | 1815 | 209 | 6924 | 659 | 334 | 993 | 28919 | 115 | 236 | 141 |
| Phase 3 average | 5 | 39 | 54 | 51 | 51 | | 15 | 57 | | 102 |

Opportunistic Infections

Opportunistic infections were detected by microbiological analysis and patients treated by HEP1 were either stable with no new infections or infections declined. For example, before treatment 38% of the patients had severe *Candida Ablicans* infection of the pharynx, after treatment only 9% were severely infected. Before treatment 52% of the patients had severe S viridans infection of the pharynx, after treat- In both groups of patients (P1-P11 and P12-P76), a general pattern of infectivity was observed in the TCID assay for detecting infectious virus particles. At the beginning of HEP1 therapy, (Phase 0-Phase 1), the load of infectious HIV virus declined sharply to low levels within the first three weeks of treatment and in 9 out of 21 patients dropped to zero for at least one week. Three patients experienced an increase in infectivity during the first week of treatment before infectivity dropped to zero in the second week. In the second phase which followed, (Phase 2), in the majority of patients HIV infectivity rose between 2× and 600× between four and eight weeks after the start of treatment. The patients reported no worsening of their condition during this period. Phase 3 followed where infectivity declined to below pre-treatment levels.

In Phase 1, the average maximum decline of virus levels below the pre-treatment baseline was minus 80%. In Phase 2, the average maximum increase of virus in Phase Two was 22 times. In Phase 3, the average maximum decline of virus below the pre-treatment baseline was minus 64%. During Phase 3, viral infectivity declined to zero in three patients. Six months after the end of treatment with HEP1, viral infectivity generally returned to pre-treatment levels.

I interpret these results as showing that the immune system was activated by HEP1 to fight HIV in Phase One. The increased level of activation in the immune system stimulated activation of a reservoir of cells latently infected with HIV leading to the increase in infectious virus in Phase 2. Finally in Phase 3, the activated immune system successfully destroyed the newly activated virus reservoir. The group of ten patients treated for only one month with HEP1 showed that the progression through Phase 2 and Phase 3 did not depend on the presence of HEP1.

HIV Viral Load by Quantitative Plasma HIV RNA PCR

Analysis of viral load was performed by the Roche labs PCR assay: Amplicor HIV-1 Monitor.

a) Lymphocytes
an average increase of 7% in absolute number of lymphocytes during treatment and an increase of 25% for the five months following treatment.

b) Leucocytes
an average increase of 10% during treatment and an increase of approximately 20% for the five months following treatment.

d) Natural Killer Cells
An average increase of 10% during treatment and an increase of approximately 30% for the five months following treatment e) B cells
An average increase of 5% during treatment and an increase of approximately 80% for the five months following treatment f) CD3 expressing cells
An average increase of 15% during treatment and an increase of approximately 30% for the five months following treatment g) CD8 expressing cells
An average increase of 15% during treatment and an increase of approximately 20% for the five months following treatment

| Patient | P1 | P2 | P3 | P4 | P5 | P6 | P7 | P8 | P9 | P10 | P11 |
|---|---|---|---|---|---|---|---|---|---|---|---|
| HIV plasmaRNA in 1000s copies/ml | 0.5 | 10 | 2 | 43 | <0.4 | 10 | 94 | 22 | 10 | 21 | <0.4 |
| re-based to 100 at start | 100 | 100 | 100 | 100 | 0 | 100 | 100 | 100 | 100 | 100 | 0 |
| Phase 0 average | | | | | | 108 | 143 | | 101 | | |
| Phase 1 average | | | 38 | 39 | 28 | 37 | 68 | 78 | 90 | 45 | |
| Phase 2 average | 476 | 197 | 103 | 64 | 28 | 223 | 112 | 110 | 1535 | 92 | |
| Phase 3 average | | 85 | 66 | 77 | 0 | 64 | 92 | 52 | | 39 | |

| Patient | P12 | P17 | P21 | P63 | P67 | P68 | P69 | P72 | P73 | P76 |
|---|---|---|---|---|---|---|---|---|---|---|
| HIV plasmaRNA in 1000s copies/ml | 13 | 11 | 11 | 4 | 230 | <0.4 | 8 | 25 | <0.4 | 9 |
| re-based to 100 at start | 100 | 100 | 100 | 100 | 100 | 0 | 100 | 100 | 100 | 100 |
| Phase 0 average | | | | | | | | | | |
| Phase 1 average | | 0 | | | 78 | | | | | 55 |
| Phase 2 average | 219 | 177 | 273 | 206 | 91 | | 142 | 191 | | 139 |
| Phase 3 average | 135 | 86 | | 98 | 63 | | 138 | 72 | | 72 |

In the majority of patients of both the one month and three month treatment, similar phases of viral suppression (Phase 1) followed by temporary viral activation (Phase 2) follow by suppression (Phase 3) were observed which was similar to the TCID data. Phase I lasted between one and four weeks and viral load declined on average by minus 47%. Phase 2 lasted between eight and forty weeks (a more sustained period than seen with the TCID assay) and viral RNA in the plasma increased on average by 3×. This was followed by Phase 3 in which viral RNA in the plasma fell below pre-treatment levels by an average reduction of minus 19%.

Cell Populations and Expression of Cell Surface Markers by Cytometry

Cells surface markers on peripheral blood mononuclear cells of the group of ten patients (P12–P76) treated for one month with HEP1 were analysed in detail using microscopy, fluorescent labelled antibodies, flow cytometry and related procedures. HEP1 treatment had the following effects on each cell populations averaged for the 10 patient group:

h) CD44-CD4 expressing cells
An average increase of 25% during treatment and an increase of approximately 60% for the five months following treatment h) CD44CD8 expressing cells
An average increase of 12% during treatment and an increase of approximately 30% for the five months following treatment i) HLA ClassI expression level on CD4 cells
An average increase of 10% during treatment and an increase of approximately 70% for the five months following treatment j) HLA ClassI expression level on CD8 cells
An average increase of 10% during treatment and an increase of approximately 70% for the five months following treatment.

k) CD25-CD8 expressing cells
An average increase of 5% during treatment from low levels and an increase of approximately 100% for the five months following treatment. CD25-CD4 cells did not show significant variation.

l) CD38-CD4 expressing cells

An average increase of 2% during treatment from low levels and a decrease of approximately 15% for the five months following treatment.

took 10 mg HEP1 orally for one month, 5 patients provided blood samples for analysis. In all of these patients it was clear that the population of CD38-CD8 cells as a percent of the total CD8 population declined toward values indicating lower risk of HIV disease and improving health.

| CD38-CD8 cells as a % CD8cells | Baseline | Month 1 treatment | Month 2 | Month 3 | Month 4 | Month 5 | Month 6 |
|---|---|---|---|---|---|---|---|
| Patient 12 | 92 | 94 | | 79 | 84 | 73 | 72 |
| Patient 17 | 66 | 71 | | 69 | 50 | 55 | 57 |
| Patient 21 | 83 | 86 | | | | 66 | |
| Patient 69 | 90 | 94 | | 86 | 79 | 71 | |
| Patient 76 | 78 | 84 | | 77 | 64 | 54 | 50 | m) CD38-CD8 expressing cells

An average increase of 2% during treatment from low levels and a decrease of approximately 25% for the five months following treatment. (the significant decrease in CD38 is discussed in the next section)

Other markers such as CD28, HLA-DR, CD45RO, CD45RA, CD57, CD62L, showed no significant changes or consistent patterns between patients.

CD38-CD8 Cells: Prognostic Indicator for Progression to AIDS

It is well recognised that the increasing size of the population of cells expressing CD38-CD8 correlates with the development of AIDS in HIV infected patients.

M Levancher, F Hulstaert, S. Tallet, S Ullery, J J Pocidalo, B A Bach (1992).

"The significance of activation markers on CD8 lymphocytes in human immunodeficiency syndrome: staging and prognostic value" Clinical Experimental Immunology 90 376–382 Briefly, the CD38-CD8 cells as a percent of the total CD8 population correlate with HIV disease progression, an observation which has been verified in a number of more recent publications. In healthy people, the percentage of the CD8 cells which also express CD38 is between 30–50%, in asymptomatic HIV infected patients is between 50–65%, in HIV infected patients with ARC is between 65% and 80% and in AIDS patients between 80% and 98%. In the follow up of the study of ten patients who Anti-HIV Antibodies in Plasma At the end of one month treatment with HEP1 of 10 patients (P12–P76), 5 patients showed significantly higher antibody titres against various HIV antigens (titres re-based to 100 before treatment).

| | Anti gp120 | Anti gp41 | Anti-p31 | Anti p24 | Anti p17 |
|---|---|---|---|---|---|
| Patient 17 | 216 | 93 | 157 | 97 | 101 |
| Patient 21 | 127 | 110 | 71 | 103 | 110 |
| Patient 63 | 110 | 131 | 387 | 146 | 154 |
| Patient 69 | 160 | 274 | 813 | 507 | 116 |
| Patient 72 | 93 | 111 | 147 | 245 | 143 |

Antibody Responses to Opportunistic Infections

HEP1 treatment stimulated antibody responses to opportunistic infections (antibody titre re-based to 100 before treatment).

| Max titre during treatment | P12 | P17 | P21 | P63 | P67 | P68 | P69 | P72 | P73 | P76 |
|---|---|---|---|---|---|---|---|---|---|---|
| Aspergillus IgG | 122 | 97 | 132 | 116 | 89 | 114 | 119 | 190 | 142 | 111 |
| Candida IgG | 127 | 100 | 126 | 170 | 447 | 51 | 293 | 214 | 120 | 129 |
| CMV IgG | 290 | 81 | 227 | 186 | 118 | 91 | 105 | 112 | 152 | 88 |
| CMV IgM | 120 | 141 | 142 | 215 | 159 | 92 | 102 | 148 | 120 | 142 |
| HSV1 IgM | 113 | 129 | 158 | 134 | 99 | 89 | 116 | 101 | 107 | 106 |
| HSV2 IgM | 107 | 129 | 109 | 108 | 156 | 158 | 146 | 111 | 300 | 186 |
| Toxoplasma IgG | 105 | 107 | 98 | 108 | 125 | 101 | 104 | 95 | 105 | 98 |

The average increase in antibody titre was plus 23% for *Aspergillus* IgG, plus 78% for *Candida* IgG, plus 50% for CMV IgG, plus 38% for CMV IgM, plus 15% for HSV1 IgM plus 51% for HSV2 IgM and plus 5% for Toxoplasma IgG.

Conclusion

The above data is consistent with the invention that a peptide with a sequence identical to part of the Hepreceptor leads to immune activation and clinical benefits in a human clinical trial of HIV patients.

EXAMPLE 4

Severe Acute and Chronic *Candida* Infection in Women can be Cured by the Immune Response Resulting from Hepreceptor Stimulation Clinical Study: Recurrent Moderate *Candida* Infection Female (age 27) with an untreated fresh out-break of *Candida* infection volunteered for the study. She reported recurrent moderate vaginal *Candida* infection (six episodes in previous twelve months) which had been previously treated with intra-vaginal application of 1% clotrimazole. She self-administered 5 ml of a 1 mg/ml solution of HEP1 intra-vaginally with a 5 ml syringe on two consecutive days. After three days all clinical symptoms of *Candida* infection had disappeared and she reported no further recurrences of *Candida* infection in the 12 month follow-up.

Clinical Study: Severe Persistent *Candida* Infection

Three female patients attending the Nearmedic Plus STD clinical in Moscow volunteered for the study who were suffering from severe *candida* infection of the vagina after they had been treated with antibiotics for various genitourinary infections. The patients were treated with 5 ml of a 2 mg/ml solution of HEP1 for three consecutive days (no other antifungal treatment was used). Comparison of microbiological analysis (cultivation of urethral, cervical canal and vaginal swabs) and clinical analysis before treatment and three weeks after treatment demonstrated either significant improvement or elimination of the infection.

peptides all increased the number of activated macrophages but Rupe111, Rupe312, Rupe411 and Rupe414 were significantly more active than HEP1.

| 1.0 microgram peptide/mouse | saline | HEP1 | Rupe111 | Rupe312 | Rupe411 | Rupe414 |
|---|---|---|---|---|---|---|
| Activated macrophages as a percent of total number of cells | 1.9 | 2.2 | 4.3 | 13.9 | 5.5 | 8.5 |

| HEP1 | SEQ ID 28 | TEKKRRETVEREKE |
| Rupe111 | SEQ ID 5: | TEKKRRETVER |
| Rupe312 | SEQ ID 8: | KKRRETVERE |
| Rupe411 | SEQ ID 11: | KRRETVER |
| Rupe414 | SEQ ID 13: | KRRETVEREKE |

| Patient | Age | Period | Clinical analysis | Urethra swab | Cervical swab | Vaginal swab |
|---|---|---|---|---|---|---|
| LLA | 34 | Before | Severe infection | Intense growth | Low growth | Low growth |
| KEM | 28 | Before | Severe infection | Intense growth | Intense growth | Intense growth |
| ALN | 35 | Before | Severe infection | Intense growth | Intense growth | Intense growth |
| LLA | 34 | After | No symptoms | Absent | Absent | Absent |
| KEM | 28 | After | mild symptoms | Low growth | few | Absent |
| ALN | 35 | After | No symptoms | Absent | Absent | Absent |

EXAMPLE 5

Rupe312, Rupe414, Rupe111 and Rupe411 Induce a Strong Macrophage Activation Response in Mice A number of peptides derived from of the Hepreceptor Domain A including HEP1 were studied in mice.

Induction of Activated Macrophages

Groups of three mice (CDAxC57B1)F1 weighing 22–24 g were injected abdominally with each peptide solution of 1.0 microgram of peptide dissolved in 0.5 ml of physiological saline. After 24 hours the animals were killed using neck vertebrae dislocation and 5 ml of Hanks solution was injected into the abdomen. The abdomen was massaged for 30 seconds and then the peritoneal liquid was collected. The collected liquid was filtered using a nylon filter into siliconised tubes containing 1.5 mg/ml EDTA.

The number of nucleus containing cells in 1 microgram of filtrate were then assessed under microscopic examination using a Nihon hemocytometer. The cells were pelleted by centrifugation for 5 minutes at 800 g, the pellet was resuspended in fetal calf serum, the cell suspension was dropped on to a glass microscope slide and dried then fixed in methanol and stained with Romanovski's colouring agent. Morphological analysis of the cells of the peritoneal exsudate were performed using an Opton optical microscope at 1600 magnifications. The number of lymphocytes, resting macrophages, activated macrophages, granulocytes and other cell types were assessed. The result was that the

EXAMPLE 6

The In Vitro Activation of Human Peripheral Blood Mononuclear Cells by Hepreceptor Peptides Demonstrated by Measuring the Incorporation of Radioactive Tritiated Thymidine into the DNA of Growing Cells Peripheral Blood Mononuclear Cells (PBMC) were separated from the peripheral blood of a healthyv donor using the standard method of fractionation in a ficoll gradient. The PBMC were suspended in culture medium containing RPMI1640 medium plus 10% fetal calf serum, 1 mM L-glutamin and antibiotics (BM). The cell suspension was placed in wells of a 96 hole microwell plate for cell cultivation, (100 microliters of suspension containing 100,000 cells per well). Then 100 microliters of BM was added containing peptide (final concentration 0.001–10 microgram/ml). The negative control well contained BM but no peptide. The plate was incubated at 37° C. for three days then radioactive $^3$H thymidine was added to a final concentration of 1 microcurie per ml. The incorporation of $^3$H thymidine into the DNA of the cells was measured using a betacounter using standard procedures. The experiment was repeated twice and the results expressed as an average of the two experiments in radioactive counts per minute. The result showed that all the peptides activate mononuclear cell proliferation but that Rupe312 and Rupe414 were significantly more active than HEP1 with peak activity around 3 nanograms/ml.

| Peptide micro g/ml | Control | HEP1 | Rupe19 | Rupe312 | Rupe414 | Rupe411 | Rupe111 | Rupe614 |
|---|---|---|---|---|---|---|---|---|
| 0.0001 | 370 | 410 | 426 | 563 | 493 | 385 | 483 | 464 |
| 0.0003 | 370 | 500 | 602 | 742 | 580 | 510 | 483 | 503 |
| 0.001 | 370 | 989 | 718 | 976 | 684 | 702 | 710 | 550 |
| 0.003 | 370 | 700 | 756 | 3222 | 2087 | 598 | 665 | 752 |
| 0.01 | 370 | 628 | 545 | 656 | 650 | 532 | 537 | 607 |
| 0.03 | 370 | 517 | 586 | 539 | 596 | 500 | 642 | 538 |
| 0.1 | 370 | 456 | 537 | 533 | 485 | 499 | 633 | 596 |
| 0.3 | 370 | 399 | 563 | 611 | 492 | 486 | 668 | 635 |
| 1 | 370 | 400 | 509 | 472 | 449 | 468 | 529 | 600 |
| 3 | 370 | 412 | 502 | 455 | 437 | 420 | 486 | 499 |
| 10 | 370 | 501 | 517 | 405 | 394 | 390 | 470 | 412 |

HEP1    SEQ ID 28   TEKKRRETVEREKE
Rupe19  SEQ ID 4:   TEKKRRETV
Rupe312 SEQ ID 8:   KKRRETVERE
Rupe414 SEQ ID 13:  KRRETVEREKE
Rupe411 SEQ ID 11:  KRRETVER
Rupe111 SEQ ID 5:   TEKKRRETVER
Rupe614 SEQ ID 18:  RETVEREKE

EXAMPLE 7

Effect of Hepreceptor Peptides on Expression of MHC Class I on Various Immunological Cells The incubation of Hepreceptor derived peptides (0.003 micrograms per ml) with human White Blood Cells (WBC) for 24 hours at 37° C., resulted in a fall in the intensity of HLA expression on the cell surface of all WBC (due to cell activation and receptor internalisation). Rupe 312 was more active than Rupe 414 which was more active than HEP1.

Data rebased to 100 for the control value in the absence of peptides

| | Density of cell surface expression of HLA Class I | | | | |
|---|---|---|---|---|---|
| | Monocytes/ Macrophages | CD8 lymphocytes | CD4 lymphocytes | B and NK cells | Granulocytes |
| Control | 100 | 100 | 100 | 100 | 100 |
| HEP1 | 83 | 83 | 80 | 84 | 89 |
| Rupe414 | 83 | 76 | 77 | 77 | 85 |
| Rupe312 | 71 | 72 | 70 | 73 | 81 |

A cell specific effect of this activation was an increase in the population of monocytes expressing MHC Class I and a decrease in the population of CD8 lymphocytes expressing MHC Class I.

Data rebased to 100 for the control value in the absence of peptides

| | Percentage of cell population expressing HLA Class I | | | | |
|---|---|---|---|---|---|
| | Monocytes/ Macrophages | CD8 lymphocytes | CD4 lymphocytes | B and NK cells | Granulocytes |
| Control | 100 | 100 | 100 | 100 | 100 |
| HEP1 | 108 | 91 | 105 | 102 | 100 |
| Rupe414 | 109 | 89 | 105 | 101 | 98 |
| Rupe312 | 119 | 85 | 104 | 105 | 98 |

(Rupe312 SEQ ID 8: KKRRETVERE and Rupe414 SEQ ID 13: KRRETVEREKE)

EXAMPLE 8

Hepreceptor Peptides Suppresses IL-8 Production in WBC

The suppressive effect of increasing concentrations of Rupe312, a Hepreceptor peptide, on the expression of IL-8 by human WBC after a 48 hour incubation at 37° C. was detected. IL-8 is a chemotactic factor that is produced in response to inflammatory stimulus which attracts and activates T cells, neutrophils, basophils, granulocytes but not monocyte/macrophages. The inhibition of IL-8 may play a role in the selective activity of Rupe 312 in activating monocytes macrophages. The measurement of IL-8 provides an assay for determining the activity of various Hepreceptor derived peptides.

| Rupe312 concentration in micrograms/ml | IL-8 concentration in culture in picrograms/ml |
|---|---|
| 0 | 18900 |
| 0.001 | 13900 |
| 0.003 | 10700 |
| 0.01 | 8984 |
| 0.03 | 7869 |
| 0.1 | 6426 |

(IL-8 E1A assay manufactured by Innogenetics, Belgium)
(Rupe312 SEQ ID 8: KKRRETVERE)

EXAMPLE 9

Very Low Dose Hepreceptor Peptides (1–100 Nanograms/Mouse) Protect Mice from Acute Infection by *Salmonella tryphimurium*

Laboratory mice (CBAxC57B1 F1 hybrids) were split into groups of five which either received 0.5 ml saline or 0.5 ml saline plus various concentrations of different Hepreceptor peptides (1, 10 or 100 nanograms). 24 hours later the mice were acutely infected with *Salmonella typhimurium* (10,000 or 100,000 bacteria injected intraperitoneally per mouse). The percent of each group of mice surviving after 20 days was recorded (lethally infected control animals were dead within three days of infection).

Percent of mouse group surviving after 20 days infection

| Peptide Code | 1000s bacteria mouse | Control 0 | Hepreceptor peptides in nanograms per mouse | | | Peptide sequence |
|---|---|---|---|---|---|---|
| | | | 1 | 10 | 100 | |
| HEP1 | 10 | 0% | 20% | 20% | 40% | TEKKRRETVEREKE |
| | 100 | 0% | 0% | 0% | 0% | |
| Rupe-15 | 10 | 0% | 20% | 40% | 40% | TEKKR |
| | 100 | 0% | 20% | 20% | 0% | |
| Rupe-1024 | 10 | 0% | 40% | 40% | 40% | EREKEQMMREKEEL |
| | 100 | 0% | 0% | 20% | 40% | |

(Rupe15 SEQ ID 3: TEKKR and Rupe1024 SEQ ID 17: EREKEQMMREKEEL and HEP1 SEQ ID 28: TEKKRRETVEREKE)

Conclusion

Hepreceptor peptides protect animals from lethal bacterial infection.

EXAMPLE 10

Very Low Dose Hepreceptor Peptides (1–1000 Nanograms/Mouse) Enhance Survival Time in Mouse Lethal Herpes Virus Infection Model Laboratory white B/P mice (five per group) were injected intraperitoneally with Hepreceptor peptide (1–1000 nanograms per mouse.) 48 hours and 24 hours before a lethal injection of herpes virus (VPG-1 strain L2) at a titre of 3.5 LD50 in 0.2 ml medium.

The average survival time in days was recorded per group of mice.

| Peptide code | Control 0 | Hepreceptor peptide in nanograms per mouse | | | | Peptide sequence |
|---|---|---|---|---|---|---|
| | | 1 | 10 | 100 | 1000 | |
| HEP1 | 10 | 18 | 19 | 27 | 28 | TEKKRRETVEREKE |

Conclusion

Hepreceptor peptides significantly enhance survival time from lethal viral infection Priority Documents UK patent application GB9921881.0, Holms R., 17th September 1999

Patent Documents

U.S. Pat. No. 5,773,573
Rupert Holms 30th June 1998

Other Publications

Ossi Turunen, Markku Sainio, Juha Jaaskelainen, Olli Carpen, Antti Vaheri (1998)
"Structure-Function relationships in the ezrin family and the effect of rumor-associated point mutations in neurofibromatosis 2 protein" *Biochimica et Biophysica Acta* 1387: 1–16

Anthony Bretscher, David Reczek and Mark Berryman (1997)
"Ezrin: a protein requiring conformational activation to link microfilaments to the plasma membrane in the assembly of cell surface structures" *Journal of Cell Science* 110: 3011–3018

Claudia Hecker, Christoph Weise, Jurgen Schneider-Schaulies. Harvey Holmes. Volker ter Meulen (1997)
"Specific binding of HIV-1 envelope protein gp120 to the structural membrane proteins ezrin and moesin." *Virus Research* 49: 215–223

M Levancher, F Hulstaert, S. Tallet, S Ullery, J J Pocidalo, B A Bach (1992)
"The significance of activation markers on CD8 lymphocytes in human immunodeficiency syndrome: staging and prognostic value" *Clinical Experimental Immunology* 90 376–382

Stephan Oehen and Karin Brduscha-Riem (1998)
"Differentiation of Naive CTL to Effector and Memory CTL: Correlation of Effector Function with Phenotype and Cell Division" *The Journal of Immunology* 161 5338–5346

SEQUENCE LISTING

<160> NUMBER OF SEQ ID NOS: 28

<210> SEQ ID NO 1
<211> LENGTH: 32
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 1

Ala Arg Glu Glu Lys His Gln Lys Gln Leu Arg Gln Gln Leu Glu
1               5                   10                  15

Thr Glu Lys Lys Arg Arg Glu Thr Val Glu Arg Glu Lys Glu Gln Met
            20                  25                  30

<210> SEQ ID NO 2
<211> LENGTH: 35
<212> TYPE: PRT
<213> ORGANISM: Artificial Sequence
<220> FEATURE:
<221> NAME/KEY: MISC_FEATURE
<223> OTHER INFORMATION: Hepreceptor Peptide

<400> SEQUENCE: 2

Met Arg Glu Lys Glu Glu Leu Met Leu Arg Leu Gln Asp Tyr Pro Glu
1               5                   10                  15

Glu Lys Thr Lys Lys Ala Glu Arg Glu Leu Ser Glu Gln Ile Gln Arg
            20                  25                  30

Ala Leu Gln
        35

<210> SEQ ID NO 3
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 3

Thr Glu Lys Lys Arg
1               5

<210> SEQ ID NO 4
<211> LENGTH: 9
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 4

Thr Glu Lys Lys Arg Arg Glu Thr Val
1               5

<210> SEQ ID NO 5
<211> LENGTH: 11
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 5

```
Thr Glu Lys Lys Arg Arg Glu Thr Val Glu Arg
1               5                   10
```

<210> SEQ ID NO 6
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 6

```
Lys Lys Arg Arg Glu
1               5
```

<210> SEQ ID NO 7
<211> LENGTH: 8
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 7

```
Lys Lys Arg Arg Glu Thr Val Glu
1               5
```

<210> SEQ ID NO 8
<211> LENGTH: 10
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 8

```
Lys Lys Arg Arg Glu Thr Val Glu Arg Glu
1               5                   10
```

<210> SEQ ID NO 9
<211> LENGTH: 11
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 9

```
Lys Lys Arg Arg Glu Thr Val Glu Arg Glu Lys
1               5                   10
```

<210> SEQ ID NO 10
<211> LENGTH: 12
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 10

```
Lys Lys Arg Arg Glu Thr Val Glu Arg Glu Lys Glu
1               5                   10
```

<210> SEQ ID NO 11
<211> LENGTH: 8
<212> TYPE: PRT
<213> ORGANISM: Artificial Sequence

```
<220> FEATURE:
<221> NAME/KEY: MISC_FEATURE
<223> OTHER INFORMATION: Hepreceptor peptide

<400> SEQUENCE: 11

Lys Arg Arg Glu Thr Val Glu Arg
1               5

<210> SEQ ID NO 12
<211> LENGTH: 10
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 12

Lys Arg Arg Glu Thr Val Glu Arg Glu Lys
1               5                   10

<210> SEQ ID NO 13
<211> LENGTH: 11
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 13

Lys Arg Arg Glu Thr Val Glu Arg Glu Lys Glu
1               5                   10

<210> SEQ ID NO 14
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 14

Arg Arg Glu Thr Val
1               5

<210> SEQ ID NO 15
<211> LENGTH: 9
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 15

Arg Glu Thr Val Glu Arg Glu Lys Glu
1               5

<210> SEQ ID NO 16
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 16

Glu Arg Glu Lys Glu
1               5
```

```
<210> SEQ ID NO 17
<211> LENGTH: 14
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 17

Glu Arg Glu Lys Glu Gln Met Met Arg Glu Lys Glu Glu Leu
1               5                   10

<210> SEQ ID NO 18
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 18

Lys Glu Glu Leu Met
1               5

<210> SEQ ID NO 19
<211> LENGTH: 13
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 19

Lys Glu Glu Leu Met Leu Arg Leu Gln Asp Tyr Glu Glu
1               5                   10

<210> SEQ ID NO 20
<211> LENGTH: 14
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 20

Lys Glu Glu Leu Met Leu Arg Leu Gln Asp Tyr Pro Glu Glu
1               5                   10

<210> SEQ ID NO 21
<211> LENGTH: 12
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 21

Glu Glu Leu Met Leu Arg Leu Gln Asp Tyr Glu Glu
1               5                   10

<210> SEQ ID NO 22
<211> LENGTH: 13
<212> TYPE: PRT
<213> ORGANISM: Artificial Sequence
<220> FEATURE:
<221> NAME/KEY: MISC_FEATURE
<223> OTHER INFORMATION: Hepreceptor peptide
```

```
<400> SEQUENCE: 22

Glu Glu Leu Met Leu Arg Leu Gln Asp Tyr Pro Glu Glu
1               5                   10

<210> SEQ ID NO 23
<211> LENGTH: 11
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 23

Glu Leu Met Leu Arg Leu Gln Asp Tyr Glu Glu
1               5                   10

<210> SEQ ID NO 24
<211> LENGTH: 12
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 24

Glu Leu Met Leu Arg Leu Gln Asp Tyr Pro Glu Glu
1               5                   10

<210> SEQ ID NO 25
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 25

Met Leu Arg Leu Gln
1               5

<210> SEQ ID NO 26
<211> LENGTH: 5
<212> TYPE: PRT
<213> ORGANISM: Artificial Sequence
<220> FEATURE:
<221> NAME/KEY: MISC_FEATURe
<223> OTHER INFORMATION: Hepreceptor peptide

<400> SEQUENCE: 26

Gln Asp Tyr Glu Glu
1               5

<210> SEQ ID NO 27
<211> LENGTH: 6
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 27

Gln Asp Tyr Pro Glu Glu
1               5

<210> SEQ ID NO 28
<211> LENGTH: 14
<212> TYPE: PRT
```

```
<213> ORGANISM: Artificial Sequence
<220> FEATURE:
<221> NAME/KEY: MISC_FEATURE
<223> OTHER INFORMATION: Hepreceptor peptide

<400> SEQUENCE: 28

Thr Glu Lys Lys Arg Arg Glu Thr Val Glu Arg Glu Lys Glu
1               5                   10
```

What is claimed is:

1. An isolated molecule that binds to the hepreceptor, wherein said molecule consists of 5 to 41 amino acids containing at least 5 consecutive amino acids of SEQ D NO:29.

2. The molecule, according to claim 1, wherein said at least 5 consecutive amino acids are located at positions 1–13 in SEQ ID NO:29.

3. The molecule, according to claim 1, wherein said molecule consists of from 5 to 14 amino acids.

4. An isolated molecule that binds to the hepreceptor, wherein said molecule consists of an amino acid sequence selected from the group consisting of:

MREKEELMLRLQDXaaEEKTKKAERELSEQI-QRALQ (SEQ ID NO:2);
EREKE (SEQ ID NO:16);
EREKEQMMREKEEL (SEQ ID NO:17);
KEELM (SEQ ID NO:18);
KEELMLRLQDYEE (SEQ ID NO:19);
KEELMLRLQDYpEE (SEQ ID NO:20);
EELMLRLQDYEE (SEQ ID NO:21);
EELMLRLQDYpEE (SEQ ID NO:22);
ELMLRLQDYEE (SEQ ID NO:23);
ELMLRLQDYpEE (SEQ ID NO:24);
MLRLQ (SEQ ID NO:25);
QDYEE (SEQ ID NO:26); and
QDYpEE (SEQ ID NO:27).

5. The molecule, according to claim 4, which consists of: MREKEELMLRLQDXaaEEKTKKAERELSEQI-QRALQ (SEQ ID NO:2).

6. The molecule, according to claim 4, which consists of: EREKE (SEQ ID NO:16).

7. The molecule, according to claim 4, which consists of: EREKEQMMREKEEL (SEQ ID NO:17).

8. The molecule, according to claim 4, which consists of: KEELM (SEQ ID NO:18).

9. The molecule, according to claim 4, which consists of: KEELMLRLQDYEE (SEQ ID NO:19).

10. The molecule, according to claim 4, which consists of: KEELMLRLQDYpEE (SEQ ID NO:20).

11. The molecule, according to claim 4, which consists of: EELMLRLQDYEE (SEQ ID NO:21).

12. The molecule, according to claim 4, which consists of: EELMLRLQDYpEE (SEQ ID NO:22).

13. The molecule, according to claim 4, which consists of: ELMLRLQDYEE (SEQ ID NO:23).

14. The molecule, according to claim 4, which consists of: ELMLRLQDYpEE (SEQ ID NO:24).

15. The molecule, according to claim 4, which consists of: MLRLQ (SEQ ID NO:25).

16. The molecule, according to claim 4, which consists of: QDYEE (SEQ ID NO:26).

17. The molecule, according to claim 4, which consists of: QDYpEE (SEQ ID NO:27).

18. A method for upregulating the immune system in a patient with cancer, Human Immunodeficiency Virus (HIV), or a bacteria infection, wherein said method comprises administering to said patient an effective amount of a molecule that binds to the hepreceptor, wherein said molecule consists of 5 to 41 amino acids containing at least 5 consecutive amino acids of SEQ ID NO:29; wherein the administration of said molecule results in upregulation of the immune system in the patient.

19. The method, according to claim 18, wherein said molecule has between 5 and 14 amino acids.

20. A method for upregulating the immune system in a patient with cancer, Human Immunodeficiency Virus (HIV), or a bacteria infection, wherein said method comprises administering to said patient an effective amount of a molecule that binds to the hepreceptor, wherein said molecule consists of an amino acid sequence selected from the group consisting of:

MREKEELMLRLQDXaaEEKTKKAERELSEQIQ-RALQ (SEQ ID NO:2);
EREKE (SEQ ID NO:16);
EREKEQMMREKEEL (SEQ ID NO:17);
KEELM (SEQ ID NO:18);
KEELMLRLQDYEE (SEQ ID NO:19);
KEELMLRLQDYpEE (SEQ ID NO:20);
EELMLRLQDYEE (SEQ ID NO:21);
EELMLRLQDYpEE (SEQ ID NO:22);
ELMLRLQDYEE (SEQ ID NO:23);
ELMLRLQDYpEE (SEQ ID NO:24);
MLRLQ (SEQ ID NO:25);
QDYEE (SEQ ID NO:26); and
QDYpEE (SEQ ID NO:27).

* * * * *

UNITED STATES PATENT AND TRADEMARK OFFICE
CERTIFICATE OF CORRECTION

PATENT NO. : 6,849,596 B1
APPLICATION NO. : 09/856070
DATED : February 1, 2005
INVENTOR(S) : Rupert Donald Holms It is certified that error appears in the above-identified patent and that said Letters Patent is hereby corrected as shown below:

Column 3,
Line 42 should read --SEQ ID 29 is an amino acid sequence of a peptide according to the present invention--.

Column 35,
Line 11, should read --
```
<210> SEQ ID NO 29
<211> LENGTH: 41
<212> TYPE: PRT
<213> ORGANISM: Artificial Sequence
<220> FEATURE:
<221> NAME/KEY: MISC_FEATURE
<223> OTHER INFORMATION: Hepreceptor peptide

<400> SEQUENCE: 29

Glu Arg Glu Lys Glu Gln Met Met Arg Glu
1               5                   10
Lys Glu Glu Leu Met Leu Arg Leu Gin Asp
11              15                  20
Xaa Glu Glu Lys Thr Lys Lys Ala Glu Arg
21              25                  30
Glu Leu Ser Glu Gln Ile Gln Arg Ala Leu
31              35                  40
Gln   --.
```

Column 35,
Line 15, "SEQ D" should read --SEQ ID--.

Signed and Sealed this

Twenty-fourth Day of July, 2007

JON W. DUDAS
*Director of the United States Patent and Trademark Office*